United States Patent [19]

Bergeret et al.

[11] Patent Number: 4,581,416

[45] Date of Patent: Apr. 8, 1986

[54] PROCESS FOR THE SYNTHESIS OF TERTIARY PHOSPHINE OXIDES AND SULFIDES, AND NEW TERTIARY PHOSPHINE OXIDES AND SULFIDES

[75] Inventors: Wilfrid Bergeret, Corbeil Essonnes; Sylvie Boileau, Paris; Jean-Claude Gautier, Ablon sur Seine; Serge Raynal, Draveil, all of France

[73] Assignee: Societe Nationale des Poudres et Explosifs, Paris Cedex, France

[21] Appl. No.: 572,958

[22] Filed: Jan. 23, 1984

Related U.S. Application Data

[62] Division of Ser. No. 339,864, Jan. 18, 1982.

[30] Foreign Application Priority Data

Jan. 19, 1981 [FR] France .................................. 81 00856

[51] Int. Cl.$^4$ .............................................. C08F 8/40
[52] U.S. Cl. ................................. 525/333.4; 525/340; 525/341; 526/278
[58] Field of Search ..................... 525/333.4, 340, 341; 526/278

[56] References Cited

U.S. PATENT DOCUMENTS

| | | | |
|---|---|---|---|
| 3,337,480 | 8/1967 | Small ................................. | 525/333.4 |
| 3,454,650 | 7/1969 | Buckler et al. ..................... | 260/606.5 |
| 3,518,311 | 6/1970 | Maier ................................. | 260/606.5 |
| 3,653,352 | 4/1972 | Kleiner et al. ............... | 260/606.5 P |
| 3,888,844 | 6/1975 | D'Alelio ........................... | 525/333.4 |
| 3,997,611 | 12/1976 | Lippsmeier et al. ......... | 260/606.5 P |
| 4,137,387 | 1/1979 | Smith ................................ | 525/333.4 |
| 4,148,981 | 4/1979 | Pellegrini, Jr. et al. .............. | 526/16 |
| 4,277,565 | 7/1981 | Oda et al. .......................... | 525/333.4 |

Primary Examiner—Joseph L. Schofer
Assistant Examiner—Bernard Lipman
Attorney, Agent, or Firm—Buckman & Archer

[57] ABSTRACT

The invention relates to processes for the synthesis of tertiary phosphine oxides and sulfides.

The process according to the invention consists, in a first step, of reacting a secondary phosphine oxide or sulfide with an optionally activated alkali metal amide, and, in a second step, of reacting the mixture obtained in the first step with an organic halide containing at least one halogenophenyl radical or one halogenomethyl group.

Tertiary phosphine oxides and sulfides are complexing agents of high stability.

2 Claims, No Drawings

PROCESS FOR THE SYNTHESIS OF TERTIARY PHOSPHINE OXIDES AND SULFIDES, AND NEW TERTIARY PHOSPHINE OXIDES AND SULFIDES

This application is a division of application Ser. No. 339,864, filed Jan. 18, 1982.

Tertiary phosphine oxides and sulfides are amongst the most stable of the organic phosphorus derivatives. This stability, together with the complexing properties of these products, make them extremely attractive. Thus, the synthesis of these compounds has formed the subject of diverse and thorough investigations.

To illustrate the diversity of the proposed methods of synthesis, there may be mentioned French Pat. No. 2,159,716 assigned to Societe Nationale des Poudres et Explosifs, which is based on the reaction of phosphorus oxychloride or $PSCl_3$ with a Grignard reagent, French Pat. No. 1,399,743, which recommends the reaction of an oxygen/$PCl_3$ mixture with the same magnesium compounds, U.S. Pat. No. 3,258,492, which uses a phosphonyl chloride, and also German Pat. No. 1,912,708, French Pat. No. 2,316,244, U.S. Pat. No. 3,997,611 and U.S. Pat. No. 4,020,110, which respectively relate to the thermal decomposition of the addition product of a dialkylphosphine oxide and an α-olefine, of a quaternary phosphonium halide, of a hydroxylated quaternary phosphonium halide and of a hydroxymethylated tertiary phosphine. Another method, involving the reaction of phosphorus with an alkyl iodide in the presence of iodine, as illustrated in French Pat. No. 2,352,824, may also be mentioned.

Another method of synthesis consists of condensing a halogeno-magnesium salt of a secondary phosphine oxide with an organic halogen derivative in accordance with the equation:

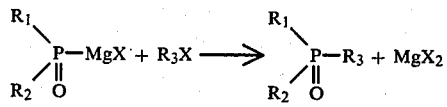

A process of this type has been described and studied, in particular by Downie and Morrs, Journal of the Chemical Society (1965), page 5,771. The disadvantage of this process lies in particular in the slowness of the reaction and in the precautions which any use of magnesium compounds necessarily involves, namely a rigorously anhydrous medium and increased safety measures due to the use of ether in bulk.

Some authors, such as Petrov et al., Zh. Obshch. Khim 30, 1,964 (1960), have therefore recommended, instead, the use of an alkali metal phosphinite according to the equation:

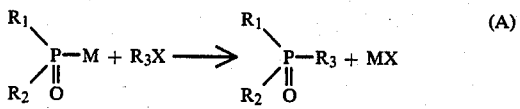

in which M=Li, Na or K.

However, these same authors do not avoid the abovementioned disadvantages because they still use a magnesium compound to prepare the said alkali metal phosphinite. In order to dispense completely with the use of a magnesium compound in this step, other authors have proposed solutions starting from phosphine oxides or sulphides:

(1) Emoto et al., Bulletin of the Chemical Society of Japan, Volume 47 (10), pages 2,449–2,452 (1974), propose the application of the reaction:

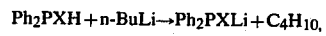

in which X=O or S.

(2) Osipenko et al., in Zhurnal Obshchei Khimii, Volume 47, No. 11, pages 2,620–2,621 (1977), start from a secondary phosphine oxide according to the equation:

(3) Horner et al., in Chemische Berichte, 94 (1961), pages 1,317–1,322, propose the reaction (which can be explosive) of an alkali metal hydride with a tertiary phosphine oxide:

These solutions can be criticised in that, in (1), n-BuLi is expensive and dangerous, in (2), potassium metal is used, which is dangerous and relatively more expensive than sodium and lithium, and in (3), it is necessary to use a high temperature (160° to 300° C. depending on the nature of M) and to start from a tertiary phosphine oxide, that is to say from a compound of the same type as that which it is ultimately intended to obtain.

Furthermore, although the prior art as a whole offers fairly satisfactory solutions for the synthesis of the alkali metal phosphinites or thiophosphinites, there remains the fact that reaction (A) according to Petrov et al. (op.cit.) has only proved entirely satisfactory hitherto in exceptionally favourable cases.

Thus, if an alkali metal diphenylphosphinite is used, there is exceptional stabilisation of the reaction intermediate, and reaction (A) is highly favoured. It is not astounding under these conditions that German Patent Specification No. 1,948,987, which uses a very reactive potassium phosphinite, makes it possible to succeed in grafting groups $R_3$, even reactive groups $R_3$, of the macromolecular type; likewise, it is not surprising that Emoto et al. (op.cit.) have done the same in the case where $R_3=CH_3$, the process being made even easier here by the use of iodide in preference to a bromide or a chloride, or that German Patent Specification No. 1,167,831, which is also restricted to diphenylphosphinous acid, permits a rapid reaction in the presence of an alkali metal alcoholate.

Using a comparable method, Osipenko et al. (op.cit.) only obtain good results when using a halide of the type $R_3X$ in which the group $R_3$ is strongly activated (a methoxy group on the α-carbon), and this is also at the expense of a very long reaction time. If, on the other hand, an organic halide in which $R_3$ is not activated is used, it is found, as by Horner et al. (op.cit.), that very long times and very high temperatures are required in order to obtain a good yield.

Finally, despite the numerous investigations carried out by research workers with very different outlooks, it must be stated that there is no known process which makes it possible easily to manufacture an alkali metal dialkylphosphinite or dialkylthiophosphinite and to facilitate the reaction of the latter with a non-activated organic halide.

It is this object, together with other advantages, in particular in respect of the costs and the safety, which the invention proposes to achieve.

This process according to the invention is a process for the synthesis of tertiary phosphine oxides or sulfides of the formula $R_1R_2R_3PZ$, in which $Z=S$ or $O$, which consists, in a first step, of obtaining an alkali metal dihydrocarbyl(thio)phosphinite of the formula $R_1R_2PZM$ from the corresponding dihydrocarbylphosphine oxide or sulfide $R_1R_2PZH$, and then, in a second step, in reacting the said alkali metal dihydrocarbyl(thio)phosphinite with an organic halide of the formula $R_3X$, characterised in that the first step is carried out by reacting an alkali metal amide of the formula $MNH_2$ with the said hydrocarbylphosphine oxide or sulfide, the second step being carried out in the presence of the unreacted part of the said alkali metal amide.

According to a variant of the process according to the invention, the alkali metal amide is activated in the form of molecular associations based on an alkali metal alcoholate, based on a salt chosen from the group comprising the thiocyanates, the cyanates, the nitrites and the cyanides of sodium, lithium or potassium, or based on an organo-alkali metal compound.

Lithium amide, sodium amide or potassium amide is preferably used as the alkali metal amide, with a particular preference for sodium amide, which is the least expensive. As the dihydrocarbylphosphine oxide or sulfide of the formula

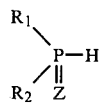

in which $Z=S$ or $O$, it is possible, in particular, to use those in which $R_1$ and $R_2$ are identical or different and are a linear or branched $C_1$ to $C_{18}$, preferably $C_1$ to $C_{12}$, alkyl group, a $C_7$ to $C_{10}$ arylalkyl group, a phenyl group or a $C_7$ to $C_{12}$ aryl group, or a $C_7$ to $C_{10}$ alkaryl group, or $R_1$ and $R_2$, taken together, form a $C_4$ to $C_9$ polymethylene chain or a $C_4$ to $C_9$ hydrocarbon chain containing at least one ethylenic unsaturation.

As the organic halide of the formula $R_3X$, it is possible, in particular, to use those in which $X=Cl$, $Br$ or $I$ and preferably those in which $X=Cl$ or $Br$, and those in which $R_3$ is an aromatic group optionally substituted by other X atoms and containing from 6 to 14 carbon atoms, or a group $CH_2R_4$, in which $R_4$ is a linear or branched primary alkyl group containing from 1 to 18 carbon atoms, a primary aralkyl group containing 7 to 14 carbon atoms, an alkaryl group containing from 7 to 14 carbon atoms or a primary alkylene group containing from 3 to 18 carbon atoms, one unsaturation not being directly bonded to X, or a group —$CH_2X$, in which X has one of the above meanings, or a group —$CH_2R_5X$, in which X has one of the above meanings and in which $R_5$ is a hydrocarbon chain containing from 1 to 18 carbon atoms, or a group

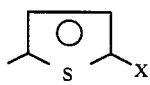

in which X has one of the above meanings, or also a crosslinked macromolecular group or a macromolecular group with a molecular weight of between 500 and 1,000,000, containing at least one other group X carried by an aromatic nucleus or a primary carbon of an aliphatic chain.

More generally, the invention is applicable to any condensation of an alkali metal (thio)phosphinite with an organic halogen derivative or organic polyhalogen derivative containing at least one halogen atom in the form of a halogenoaryl group or halogenomethyl group.

If the organic halogen derivative is a macromolecule, it can be chosen, in particular, from the group comprising chloromethylated polystyrene, poly-(p-bromostyrene), poly-(p-chlorostyrene), bromopolybutadiene, and copolymers containing the latter polymers, such as a Merrifield resin, that is to say an optionally partially crosslinked, random copolymer of styrene and a p-halogenomethylstyrene, which is moreover described in detail in French Application No. 79/31,917 of Dec. 28, 1979, filed in the name of the Applicant Company. Another example is the polymer, carrying bromopolymethylene groups and derived from polystyrene, which is obtained by Tundo and described by this author in Chemical Communications 1978, 315.

The molar proportion of alkali metal amide to be used, relative to the dihydrocarbylphosphine oxide (or sulfide) is equal to at least the stoichiometric proportion and is preferably between 1.1 and 6 times this stoichiometric proportion, the maximum apparently being 20 times. In other words, according to the invention, between 1 and 20 mols and preferably from 1.1 to 6 mols of alkali metal amide are used per mol of dihydrocarbylphosphine oxide (sulfide).

The proportion of dihydrocarbylphosphine oxide (or sulfide) to be used, relative to the organic halogen derivative, is generally consistent with the stoichiometry, that is to say one mol of oxide (or sulfide) per mol of halogen. However, depending on whether or not it is desired to effect complete substitution of the halogen atoms in the organic halogen derivative, it is possible to use between 0.1 and 20, preferably between 0.5 and 3, mols of oxide (or sulfide) per mol of halogen, a larger excess of oxide (or sulfide) corresponding to a particularly high degree of substitution, especially in the case of macromolecular halogen derivatives.

Although the presence of a solvent does not seem to be essential during each step of the process according to the invention, it is nevertheless wholly desirable. It is possible, in particular, to use a non-polar or polar, aprotic inert solvent, or a mixture of such solvents, as the solvent medium. A suitable solvent is tetrahydrofuran, but it is possible to use less polar solvents such as aliphatic or aromatic hydrocarbons, in particular toluene, xylenes and hexane. Solvents which are sensitive in a strongly basic medium, and halogen-containing solvents, should preferably be avoided.

The temperature of the reaction medium during each of the steps is advantageously ambient temperature, in strong contrast with the majority of the earlier processes. Good results during the first step are only obtained by adopting a temperature between $-20°$ and $+70°$ C., preferably between $15°$ and $50°$ C. The second step is advantageously carried out at between $-20°$ and $+100°$ C., preferably at between $10°$ and $60°$ C. Under these conditions, the first step can be completed within a period of time of between a few minutes and 3 hours and the second step can be completed within a few minutes to about ten hours for the most intractable cases in which the steric hindrance is very considerable around the halogen atom or around the (thio)phosphinite group.

In general, it is advantageous to carry out the reaction using suitably dried reactants and under an inert atmosphere, although the alkali metal amide can act as an effective and inexpensive desiccant without the process suffering as a result. However, in the latter case, it is appropriate to provide an additional excess of alkali metal amide which is sufficient to neutralise the residual moisture found in the medium.

According to the invention, the alkali metal amide can be used in an activated form. It is known that alkali metal amides form, with a very large number of hydroxyl derivatives, very reactive bases which have been referred to as complex bases. French Pat. Nos. 2,354,834 and 2,410,005, granted to Societe Nationale des Poudres et Explosifs, provide a very complete illustration of the main complex bases which are known and which can be used industrially. According to the invention, the complex base is formed in a known manner and the dihydrocarbylphosphine oxide or sulfide is added to this complex base, after which the second step is carried out as described above. As complex bases which are particularly preferred within the scope of the invention, there may be mentioned those prepared from sodium amide and a tertiary, secondary or primary aliphatic alcohol or polyoxyethylene glycol monoethers.

It is also known that alkali metal amides form, with the thiocyanates, the cyanates, the nitrites and the cyanides of the main alkali metals, very reactive bases which have been referred to as saline bases. French Pat. No. 2,430,428, granted to Societe Nationale des Poudres et Explosifs, provides a very complete illustration of the method of preparation of such saline bases. According to the invention, the saline base is formed in a known manner and the secondary phosphine oxide or sulfide is added to this saline base, after which the second step is carried out as described above. Particularly preferred saline bases which may be mentioned are those prepared from sodium amide and potassium thiocyanate or, to a lesser extent, potassium nitrite.

According to the invention, the alkali metal amide can also be activated in the form of a molecular association with an organo-alkali metal compound of the type described as claimed in a patent application filed in France on the same day as the present application and entitled "New associations of bases resulting from the association of an alkyl-lithium compound or aryllithium compound with an alkali metal amide or hydride, polymerisation process in which they are used, and product obtained".

These molecular associations can all be used within the scope of the present invention. However, those which are more particularly preferred are the ones involving an additional cation effect, which consists in mixing an alkyl-alkali metal compound with an amide of another alkali metal. Thus, sodium amide being the preferred amide, it is advantageously associated with an alkyl-lithium compound such as n-butyl-lithium. According to the invention, the molecular association alkali metal amide/organo-alkali metal compound is formed as described in the abovementioned application and the alkali metal (thio)phosphinite is added to the said association, or vice versa, after which the second step is carried out as described above.

The yields of the process according to the invention are generally very high and are fairly dependent on various choices, namely the nature of the amide used, the reaction temperature, the solvent used, the nature of the hydrocarbon groups carried by the secondary phosphine oxide or sulfide, and the nature of the organic halogen derivative. Furthermore, if the organic halogen derivative is a polymer, it is not always advantageous to obtain a very high degree of substitution.

The invention also relates, by way of new industrial products, to polymers carrying groups $R_1R_2PZ$— (in which $Z=S$ or $O$) and derived from halogen-containing polymers in which the halogens are not highly activated as regards their condensation with an alkali metal (thio)phosphinite. It had been impossible to obtain these polymers hitherto by the known processes, and they are derived respectively from p-halogenopolystyrenes and from polystyrenes which are optionally partially crosslinked and which carry groups of the type $—CH_2{-}_pX$, the said polymers being of the general formulae (I) and (II):

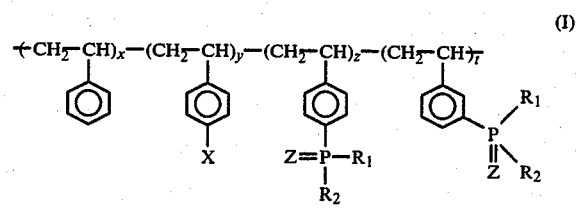

in which x, y, z and t are numbers such that $x+y+z+t=1$, $0<x<0.9$, $0<y<0.5$, $0.03<z<1.0$ and $0<t/z<0.4$, Z being an oxygen or sulphur atom, X being a chlorine or bromine atom and $R_1$ and $R_2$ being linear or branched $C_1$ to $C_{18}$ alkyl groups, preferably $C_1$ to $C_{12}$ groups and in particular octyl groups in both cases, for a number-average molecular weight $\overline{Mn}$ such that $20,000<\overline{Mn}<1,000,000$.

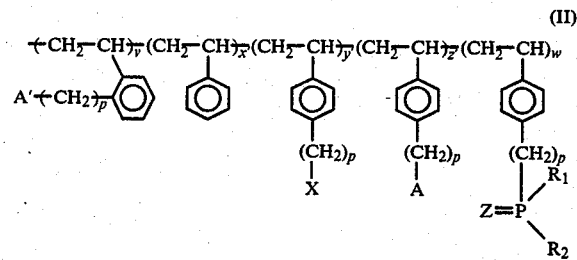

in which $2<p<12$, v, w, x', y' and z' are numbers such that $v+w+x'+y'+z'=1$, $v/y'+z'+w<0.1$, $0<x'<0.7$, $0<y'<0.4$, $0<z'<0.1$ and $0.03<w<0.9$, $X=Cl$ or Br, $Z=O$ or S, $R_1$ and $R_2$ are identical or different and are a linear or branched $C_1$ to $C_{18}$, preferably $C_1$ to $C_{12}$, alkyl group or a $C_7$ to $C_{10}$ arylalkyl group, and A is a phenyl nucleus of a polystyrene chain of the same type, the groups A' being in some cases a group X and in other cases a group $—PZR_1R_2$, Z, X, $R_1$ and $R_2$ having the above meanings.

The various aspects of the invention and also the advance which can thereby be achieved will be understood more clearly with the aid of the following non-limiting examples.

EXAMPLES 1 TO 9

Synthesis of Tertiary Phosphine Oxides

In a 250 ml reactor fitted with a stirrer, the complex base $NaNH_2/t\text{-}BuONa$ was prepared in a conventional manner by placing 100 millimols of NaNH$_2$, 35 millimols of t-butyl alcohol and 30 ml of tetrahydrofuran in the reactor. The heterogeneous mixture was heated for 30 minutes at 40° C., whilst stirring, and the said mixture was then kept at the same temperature for a further 30 minutes, after which a solution of 33 millimols of dioctylphosphine oxide (DOPO) in 50 ml of THF was run into the said mixture. Two hours after the start of the introduction, the reaction is complete and the presence of sodium phosphinite and also the disappearance of the DOPO are observed by I.R. spectroscopy. This reaction time is much shorter than that required by the method using sodium metal; furthermore, it is unnecessary to heat the reaction mixture at the reflux temperature of the solvent.

The second step of the process was then carried out by reacting various organic halogen compounds with portions of the solution of alkali metal phosphinite obtained in the first step. The molar proportion alkali metal phosphinite/functional groups in the halogen derivative was 1 for Examples 1 to 9 respectively.

The results obtained are collated in the following table:

| Example No. | Halogen derivative | Product obtained (and yield in %) | Observations |
|---|---|---|---|
| 1 | C$_6$H$_5$—Br | C$_6$H$_5$—P(Oct)$_2$ (=O) (>50) (a) | Melting point = 41–42° C. (literature: 42–43° C.) Analysis by $^{13}$C NMR. |
| 2 | n-C$_8$H$_{17}$Cl | (C$_8$H$_{17}$)$_3$PO (>60) (a) | Melting point = 51° C. (literature: 51–51.5° C.) Analysis by $^{13}$C NMR. |
| 3 | Cl(CH$_2$CH$_2$O)$_3$Bu | (oct)$_2$P(=O)—CH$_2$—CH$_2$—P(=O)(oct)$_2$ | Melting point = 152° C. (literature: 152–152.50° C.) Analysis by mass spectroscopy. |
| 4 | Br(CH$_2$)$_3$Br | (Oct)$_2$P(=O)(CH$_2$)$_3$P(=O)(Oct)$_2$ (>65) (a) | Melting point = 91° C. (literature: 145–150° C.) (b) Analysis by mass spectroscopy. Analysis by $^{13}$C NMR. Elementary analysis:     C    H    O    P Found  70.93 12.14 5.07 10.47 Theory 71.43 12.59 5.44 10.54 |
| 5 | Br(CH$_2$)$_4$Br | (Oct)$_2$P(=O)(CH$_2$)$_4$P(=O)(Oct)$_2$ (80) | (c) |
| 6 | Br(CH$_2$)$_5$Br | (Oct)$_2$P(=O)(CH$_2$)$_5$P(=O)(Oct)$_2$ (82) | (c) |
| 7 | Br(CH$_2$)$_6$Br | (Oct)$_2$P(=O)(CH$_2$)$_6$P(=O)(Oct)$_2$ (78) | (c) |
| 8 | C$_6$H$_5$—CH$_2$—Cl | (Oct)$_2$P(=O)(CH$_2$)—C$_6$H$_5$ (>50) (a) | Melting point = 55° C. Confirmation by $^{13}$C NMR. |
| 9 | 1-bromonaphthalene | (Oct)$_2$PO—naphthyl (75) | (d) |

(a) of non-recrystallised product.
(b) the literature value is questioned because of the consistency of the spectra with the spectral and elementary analyses.
(c) structure confirmed both by mass spectroscopy and by $^{13}$C NMR.
(d) this gave 25% of the α-naphthyl derivative and 75% of the β-naphthyl derivative, which were separated by chromatography on an alumina column.

The same procedure was applied to 2-chloropropane, 2-bromopropane, bromobutane, t-butyl chloride and cyclohexyl bromide (Examples 10 to 14). No reaction was observed; thus, the process can only be applied essentially to aromatic halogen derivatives or to aliphatic or araliphatic derivatives in which at least one halogen atom is carried by a primary carbon. The process was thus applied successfully to $BrCH_2Br$ and

with which, however, expected, totally phosphorus-substituted products were obtained in a mixture with mono-substituted products, this being explained by the fact that the abovementioned ratio DOPO/X was maintained (Examples 15 and 16).

Furthermore, the process proved to be applicable to secondary phosphine sulfides, in particular $Ph_2PSH$, the yields being less good and mixtures being more easily obtained than with the oxides, all other conditions being equal.

lents of DOPO/equivalents of Br have been indicated for each experiment.

Bromopolystyrenes, grafted by dioctylphosphine oxide groups, were obtained in solution in THF. The polymers were recovered by precipitation in methanol, which eliminated the excess DOPO present.

These polymers, which are soluble in THF, toluene and chloroform, have the formula:

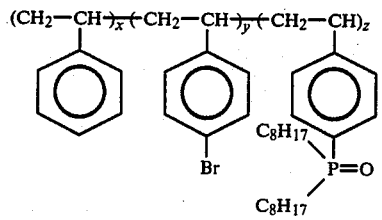

The characteristics of the polymers obtained are collated in the following table:

| Example No. | Molar ratio DOPO/Br | Duration (hours) | Mn (osmometry) | % C | % H | % O | % P | % Br | % y | % z |
|---|---|---|---|---|---|---|---|---|---|---|
| 17 | 14 | 4 | 187,000 | — | — | — | 3.25 | 2.52 | 4.5 | 15.8 |
| 18 | 6 | 4 | — | — | — | — | 4.54 | 1.50 | 3.3 | 26.0 |
| 19 | 6 | 4 | 265,000 | 83.99 | 8.94 | 2.25 | 3.47 | 1.56 | 3.0 | 17.1 |
| 20 | 1.2 | 4 | 140,000 | 69.09 | 6.04 | | 0.85 | 23.13 | 43.1 | 4.1 |

EXAMPLES 17 TO 20

Synthesis of Polystyrenes Carrying Dioctylphosphine Oxide Groups

The procedure of the preceding examples was repeated using bromopolystyrenes of the formula:

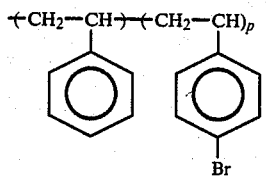

as the halogen derivatives.

Polymer A contained 12.48% by weight of Br, that is to say p=18.5%, and had an $M_n$ of 133,000 (by osmometry).

Polymer B contained 18.8% by weight of Br, that is to say p=30%, and had an $M_n$ of 50,000 (by gel permeation chromatography).

Polymer C, having a molecular weight $M_n$ of 184,000 (osmometry), contained 77.43% of C, 6.58% of H and 14.06% by weight of Br, that is to say p=21.2%.

Polymer D, having a molecular weight $M_n$ of 130,000 (osmometry), contained 66.84% of C, 5.42% of H and 27.24% of Br, that is to say p=48.4%.

These polymers are obtained by brominating polystyrene in $CCl_4$, in the presence of anhydrous $FeCl_3$, the polystyrene itself being obtained by anionic polymerisation of the monomer in THF, at low temperature, the polymerisation being initiated by naphthalene-sodium.

A solution of alkali metal phosphinite obtained in accordance with the same procedure as in Examples 1 to 9 was reacted with solutions of polymers A to D in THF: the reaction time allowed and the ratio equiva- Examples 17 to 20 were carried out using polymers A, B, C and D respectively. It was possible to show by NMR that a small proportion (less than 30% of the total) of the dioctylphosphine oxide groups were attached in the meta-position of the phenyl groups.

It is seen that an increase in the degree of substitution of the Br by the phosphorus groups is favoured by an increase in the excess of secondary phosphine oxide. This degree can easily be varied from 10 to 90% according to the preceding examples.

EXAMPLES 21 AND 22

Synthesis of Crosslinked Polymers Carrying DEPO and DOPO Groups

The procedure of Examples 17 to 20 (but carried out at 50° C.) was applied to a macroporous bromopolystyrene marketed by ALDRICH under the name Brominated macroporous Polystyrene. This resin, crosslinked with 3% of divinylbenzene, contains from 3 to 4.5 milliequivalents of Br per gram.

10 g of this resin were swollen in 10 ml of THF for 24 hours before the process according to the invention was applied.

A ratio secondary phosphine oxide/halide of 6 was used, based on 4.5 milliequivalents of Br per g of resin.

Diethylphosphine oxide (DEPO) and dioctylphosphine oxide (DOPO) were used in Experiments 21 and 22 respectively. The reaction times are 4 hours.

This gave crosslinked polystyrenes carrying residual p-bromophenyl groups and carrying dialkylphosphine oxide groups in the para-position of phenyl groups. The chemical characteristics of these polymers are shown in the following table:

| Example No. | Phosphorus unit | Br % by weight | P % by weight | Milli-equivalents of P per g of resin | Degree of sub-stitution |
|---|---|---|---|---|---|
| 21 | -(CH$_2$-CH)- with phenyl ring, O=P Et$_2$ | 27.93 | 1.78 | 0.57 | 6.0% |
| 22 | -(CH$_2$-CH)- with phenyl ring, O=P Oct$_2$ | 23.86 | 1.65 | 0.53 | 6.5% |

Although low, the degrees of substitution obtained are nonetheless remarkable because it had hitherto been extremely difficult to initiate substitution using conventional methods, in the case of polymers as highly crosslinked as those used in the two Experiments 21 and 22.

EXAMPLE 23

4 g of sodium amide and 50 ml of THF were placed in a 250 ml reactor. When the medium obtained had been heated to 40° C., 9 g of DOPO were run into the stirred reactor in the course of 30 minutes.

With the temperature kept at 40° C., 16.5 millimols of 1,4-dibromobutane, that is to say a ratio equivalents of DOPO/equivalents of Br of 1, were run into the resulting mixture in the course of 30 minutes. The reaction was left to reach completion for half an hour at 40° C. and the reaction mixture was precipitated in water. The organic phase was extracted into 100 ml of chloroform and, after evaporation, 9.3 g of crude product were collected (yield: 94%). The product was recrystallised from hexane and 6.8 g of a product having a melting point of 95° C. were collected (yield: 69%). The product was identified by its I.R. and NMR spectra as corresponding to the formula (Oct)$_2$PO(CH$_2$)$_4$PO(Oct)$_2$.

EXAMPLES 24 AND 25

The preceding example shows that, in THF, sodium amide by itself is as reactive towards the secondary phosphine oxide as the amide activated in the form of a complex base (compare Example 5).

In a solvent of low polarity, which is substantially less polar than THF, a comparative kinetic study of the reaction of DOPO with octyl chloride, on the one hand in the presence of amide by itself and on the other hand in the presence of amide activated in the form of a complex base, was carried out.

The initial amounts are those of Example 1 (33 millimols of sodium amide in both cases and 33 millimols of diethylene glycol monoethyl ether) and the solvent was toluene.

The octyl chloride was present in a 15 mol % excess relative to the DOPO. The reaction was followed by gas phase chromatography. The results obtained are collated in the following table:

| Example No. | Reactant | Degree of conversion (in %) after | | | | |
|---|---|---|---|---|---|---|
| | | 0.5 hour | 1.0 hour | 1.5 hours | 2.0 hours | 2.5 hours |
| 24 | NaNH$_2$ by itself | 6 | 11 | 15 | 20 | 28 |
| 25 | NaNH$_2$/Et(OCH$_2$CH$_2$)$_2$ONa | 9 | 40 | 59 | 78 | 82 |

It is seen that the use of activated amide makes it possible to accelerate the reaction when it is carried out in a solvent of low polarity.

EXAMPLES 26 to 33

Sodium amide activated by means of an organoalkali metal compound was used here. To do this, the association alkali metal amide/organo-alkali metal compound was first prepared in 50 ml of solvent (THF or toluene, see table), at ordinary temperature, by introducing 25 millimols of sodium amide and 23 millimols of butyllithium (Examples 26 to 31), 25 millimols of methyllithium (Example 32) or 25 millimols of phenyl-lithium (Example 33) into a 250 ml reactor. 20 millimols of secondary phosphine oxide (diphenylphosphine oxide in Examples 26 to 31 and dioctylphosphine oxide in Examples 32 and 33) were then immediately run into the resulting mixture, in the course of ten minutes and whilst stirring. When the addition had ended, the mixture was left for a further 2 hours at 20° C., whilst stirring. The organic halogen derivative indicated in the table (10 millimols) was added to the resulting reaction mixture in the course of 2 hours, whilst stirring and still at 20° C. The results obtained are reported in the following table:

| Example | Halogen derivative | Solvent | Product obtained | Characterisation |
|---|---|---|---|---|
| 26 | Br—CH$_2$—Br | THF | Ph$_2$POCH$_2$POPh$_2$ | by MS (a) |
| 27 | Br(CH$_2$)$_3$Br | THF | Ph$_2$PO(CH$_2$)$_3$POPh$_2$ | by MS (a) |
| 28 | Br(CH$_2$)$_4$Br | THF | Ph$_2$PO(CH$_2$)$_4$POPh$_2$ | by MS (a) |
| 29 | Br(CH$_2$)$_5$Br | THF | Ph$_2$PO(CH$_2$)$_5$POPh$_2$ | by NMR (b) |
| 30 | Br(CH$_2$)$_6$Br | THF | Ph$_2$PO(CH$_2$)$_6$POPh$_2$ | by NMR (b) |
| 31 | naphthyl-Br | PhCH$_3$ | Ph$_2$PO-naphthyl and | by NMR (b) and MS (a) |

| Example | Halogen derivative | Solvent | Product obtained | Characterisation |
|---|---|---|---|---|
| 32 | ![Br-CH=CH-S-CH=CH-Br structure] | PhCH₃ | 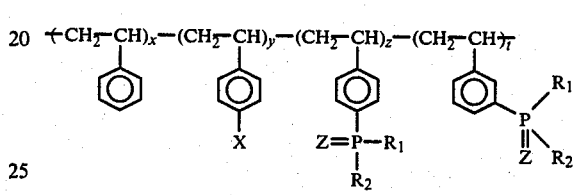 | by NMR (b) and MS (a) |
| 33 | Br(CH₂)₆Br | PhCH₃ | Oct₂PO(CH₂)₆POOct₂ | by NMR (b) and MS (a) |

(a) Analysis by mass spectroscopy, verification that the expected peaks are obtained.
(b) Analysis by ¹³C nuclear magnetic resonance.

EXAMPLE 34

4 g (100 millimols) of sodium amide in 30 ml of toluene were placed in a 250 ml reactor, this mixture was heated for 2 hours at 40° C., 9 g (33 millimols) of DOPO in 60 ml of toluene were then added and the mixture was heated for 2 hours at 40° C., whilst stirring.

The I.R. spectrum of the resulting mixture shows that sodium dioctylphosphinite has been formed.

33 millimols of Br(CH₂)₄Br are added to the reaction mixture and the reaction is left to proceed for 1 hour at 40° C., whilst stirring. The degree of conversion obtained after this time is 20%.

EXAMPLES 35 and 36

100 millimols of sodium amide and 50 millimols of sodium thiocyanate in 30 ml of toluene were placed in a 250 ml reactor. The mixture was stirred for 2 hours at 40° C., after which a solution of 35 millimols of DOPO in 60 ml of toluene was added to the resulting medium.

The reaction mixture was stirred for 2 hours at 40° C. A composition containing sodium dioctylphosphinite and not showing a P-H band in the infra-red spectrum (no residual phosphine oxide) was then obtained.

Br(CH₂)₄Br (33 millimol-equivalents of bromine) was then added to this composition and the reaction was left to proceed for 1 hour at 40° C.

The reaction medium obtained was precipitated in water, the organic phase was extracted with chloroform and the chloroform extract was then dried with MgSO₄. After evaporation of the solvent and then recrystallisation from hexane, 6.3 g of 1,4-di-(dioctylphosphine oxide)-butane were obtained, that is to say a yield of 65% of purified product (melting point: 99°–99.5° C.).

A comparable result was obtained on replacing KSCN by NaNO₂ (the yield is slightly lower).

We claim:

1. By way of a new product, the substituted polystyrene of the formula

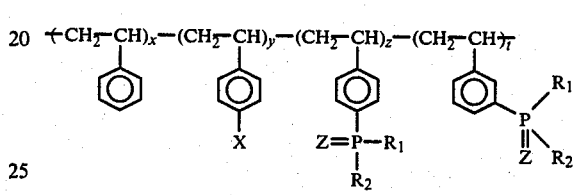

(I)

in which x, y, z and t are numbers such that $x+y+z+t=1$, $0<x<0.9$, $0<y<0.5$, $0.03<z<1.0$ and $0<t/z<0.4$, Z being a sulphur or oxygen atom, X being a chlorine or bromine atom and $R_1$ and $R_2$ being linear or branched $C_1$ to $C_{18}$ alkyl groups, preferably $C_1$ to $C_{12}$ groups and in particular octyl groups in both cases, for a number-average molecular weight $\overline{Mn}$ such that $20,000<\overline{Mn}<1,000,000$.

2. By way of a new product, the substituted polystyrene of the formula

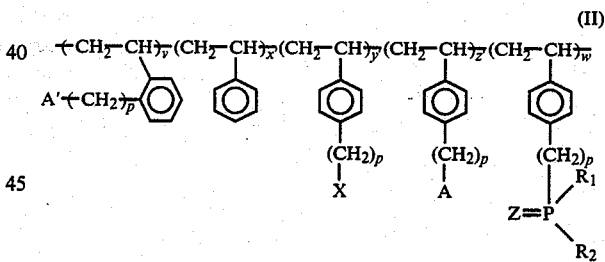

(II)

in which $2<p<12$, v, w, x′, y′ and z′ are numbers such that $v+w+x'+y'+z'=1$, $v/y'+z'+w<0.1$, $0<x'<0.7$, $0<y'<0.4$, $0<z'<0.1$ and $0.03<w<0.9$, X=Cl or Br, Z=O or S, $R_1$ and $R_2$ are identical or different and are a linear or branched $C_1$ to $C_{18}$, preferably $C_1$ to $C_{12}$, alkyl group or a $C_7$ to $C_{10}$ arylalkyl group, and A is a phenyl nucleus of a polystyrene chain of the same type, the groups A′ being in some cases a group X and in other cases a group $-PZR_1R_2$, Z, X, $R_1$ and $R_2$ having the above meanings.

* * * * *